(12) United States Patent
Genet et al.

(10) Patent No.: US 6,306,179 B1
(45) Date of Patent: Oct. 23, 2001

(54) METHOD FOR THE SYNTHESIS OF 2-HYDROXYALKYL-PARA-PHENYLENEDIAMINES, NEW 2-HYDROXYALKYL-PARA-PHENYLENEDIAMINES, THEIR USE FOR OXIDATION DYEING, DYEING COMPOSITIONS AND METHODS OF DYEING

(75) Inventors: Alain Genet, Aulnay sous Bois; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/177,192

(22) Filed: Oct. 22, 1998

(30) Foreign Application Priority Data

Oct. 22, 1997 (FR) .................................................. 97 13241

(51) Int. Cl.$^7$ ............................. A61K 7/13; C07C 211/51
(52) U.S. Cl. ...................... 8/406; 8/410; 8/649; 564/440; 564/442; 564/443
(58) Field of Search ................................ 8/406, 407, 408, 8/410, 416, 649; 564/440, 442, 443, 305

(56) References Cited

U.S. PATENT DOCUMENTS

| | | | |
|---|---|---|---|
| 2,273,564 | 2/1942 | Dickey et al. ...................... 560/251 |
| 4,840,639 | 6/1989 | Husemeyer et al. ..................... 8/410 |
| 5,514,188 | * 5/1996 | Cotteret et al. .......................... 8/410 |
| 5,529,584 | * 6/1996 | Audousset et al. ...................... 8/416 |
| 5,599,353 | * 2/1997 | Cotteret et al. .......................... 8/416 |
| 5,620,484 | * 4/1997 | Maubru .................................. 8/416 |
| 5,752,983 | 5/1998 | Audousset et al. ...................... 8/409 |

FOREIGN PATENT DOCUMENTS

| | | |
|---|---|---|
| 3 441 148 | 5/1986 | (DE) . |
| 0 007 537 | 2/1980 | (EP) . |
| 0 722 710 | 7/1996 | (EP) . |
| 2 630 438 | 10/1989 | (FR) . |
| 2 647 341 | 11/1990 | (FR) . |

OTHER PUBLICATIONS

Weissberger, "Process for Dyeing Pelts, Hairs and Feathers," 1 page, Nov. 1951.*

English Language Derwent Abstract of DE 3 441 148, 5/86.
English Language Derwent Abstract of FR 2 647 341, 11/90.
English Language Derwent Abstract of FR 2 630 438, 10/89.

Sudhirchandra Niyogy, "Organo–Metalloid Compounds. Part II.", Proc. Indian Acad. of Sciences, vol. IV(A), 1937, pp. 309–313.

L.K.J. Tong et al., "The Mechanism of Dye Formation in Color Photography. VII. Intermediate Bases in the Deamination of Quinonediimines", Journal of the American Chemical Society, vol. 82, No. 8, Apr. 25, 1960, pp. 1988–1996.

R.L. Bent et al., "Chemical Constitution, Electrochemical, Photographic and Allergenic Properties of p–Amino–N–dialkylanilines", Journal of the American Chemical Society, vol. 73, 1951, pp. 3100–3125.

* cited by examiner

*Primary Examiner*—John Hardee
(74) *Attorney, Agent, or Firm*—Finnegan, Henderson, Farabow, Garrett & Dunner, L.L.P.

(57) ABSTRACT

The present invention relates to a new method for the synthesis of 2-hydroxyalkyl-para-phenylenediamines which are substituted or unsubstituted at the 5-position of the benzene ring, new 2-hydroxyalkyl-para-phenylenediamines which are substituted or unsubstituted at the 5-position of the benzene ring, their use for the oxidation dyeing of keratinous fibers, the dyeing compositions containing them, as well as the methods of dyeing using them.

25 Claims, No Drawings

METHOD FOR THE SYNTHESIS OF 2-HYDROXYALKYL-PARA-PHENYLENEDIAMINES, NEW 2-HYDROXYALKYL-PARA-PHENYLENEDIAMINES, THEIR USE FOR OXIDATION DYEING, DYEING COMPOSITIONS AND METHODS OF DYEING

The present invention relates to a new method for the synthesis of 2-hydroxyalkyl-para-phenylenediamines which are substituted or unsubstituted at the 5-position of the benzene ring, new 2-hydroxyalkyl-para-phenylenediamines which are substituted or unsubstituted at the 5-position of the benzene ring, their use for the oxidation dyeing of keratinous fibers, the dyeing compositions containing them, as well as the methods of dyeing using them.

It is known to dye keratinous fibers, in particular human hair, with dyeing compositions containing appropriate oxidation dye precursors, in particular ortho- or para-phenylenediamines, ortho- or para-aminophenols, heterocyclic compounds such as diaminopyrazole derivatives, generally called oxidation bases. The oxidation dye precursors, or oxidation bases, are colorless or weakly colored compounds which, combined with suitable oxidizing agents, can give rise, by a process of oxidative condensation, to colored and coloring compounds.

It is also known that the shades obtained with these oxidation bases can be varied by combining them with couplers or color modifiers, the latter being chosen especially from aromatic meta-diamines, meta-aminophenols, meta-diphenols and certain heterocyclic compounds.

The variety of molecules used as regards oxidation bases and couplers allows a rich palette of colors to be obtained.

Among all the oxidation bases cited above, one family which is very widely used is that of the para-phenylenediamines. The para-phenylenediamines can be provided in the form of compounds which are variously substituted on the benzene ring, in particular in the form of 2-hydroxyalkyl-para-phenylenediamines exhibiting advantageous dyeing qualities.

The dyeing compositions containing these particular para-phenylenediamines and optionally one or more couplers indeed make it possible to obtain colors with a variety of shades, of the desired intensity, and exhibiting good behavior in relation to external agents (light, adverse weather conditions, washing, permanent waving, perspiration, rubbing).

FR-A-2,647,341 discloses 2-(2,5-diaminophenyl)ethanol and its use in oxidation coloration. DE-A-3,441,148, at page 9, discloses up to the compound produced by step 3 in the scheme below. The DE application, however, does not teach the reduction reaction shown in the scheme immediately following below.

SYNTHESIS SCHEME

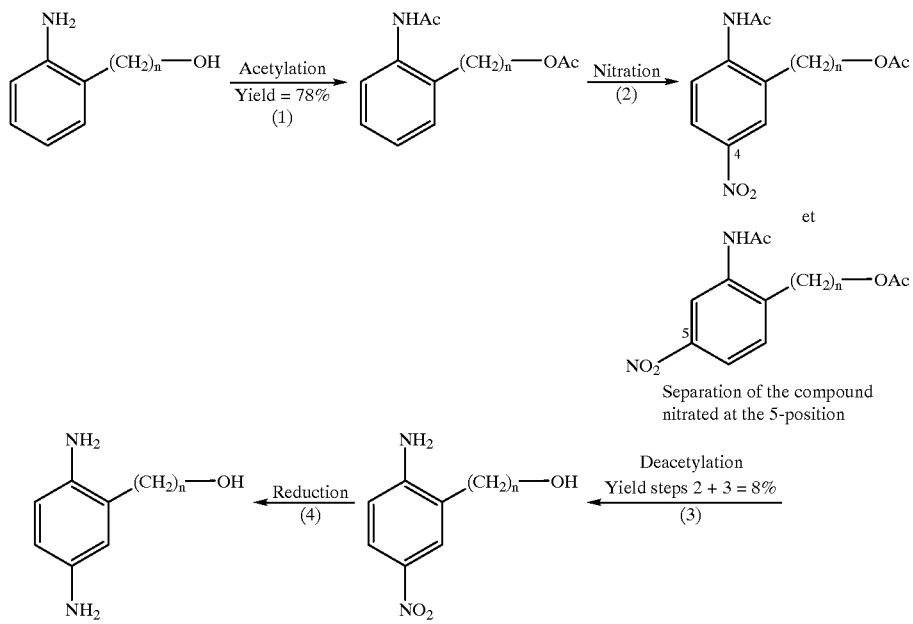

The yields which appear in this reaction scheme relate to the compounds in which n=2.

The method of synthesis described in this prior art scheme has, however, a major disadvantage since the step (2) of nitration leads to a mixture of compounds nitrated at the 4-position and of compounds nitrated at the 5-position, and only a small portion of the starting acetylated 2-hydroxyalkylanilines is converted to compounds nitrated at the 4-position of the benzene ring (that is to say 8%, after separation of the compounds nitrated at the 5-position, for the compounds in which n=2). This low yield and the need to carry out a separation of the nitrated isomers are not acceptable at the industrial level.

Furthermore, this prior art method of synthesis does not make it possible to arrive at 2-hydroxyalkyl-para-phenylenediamines capable of having a substitution at the 5-position of the benzene ring.

It was during the search to overcome these problems that the applicant discovered the method which is the subject of the invention.

The first subject of the invention is therefore a new method for the synthesis of 2-hydroxyalkyl-paraphenylenediamines which are substituted or unsubstituted at the 5-position of the benzene ring and of their addition salts with an acid, characterized in that it comprises at least the following steps:

Step No. 1: the amine function at the 1-position of the benzene ring and the alcohol function at the 2-position of the benzene ring of a 2-hydroxyalkylaniline which is substituted at the 5-position of the benzene ring with a halogen atom or with a $C_1$–$C_6$ alkyl radical are protected;

Step No. 2: a reaction of nitration at the 4-position of the benzene ring is carried out on the compound obtained in Step No. 1;

Step No. 3: the amine function at the 1-position of the benzene ring and the alcohol function at the 2-position of the benzene ring of the compound obtained in Step No. 2 are deprotected;

Step No. 4: a reaction of reduction of the nitro group at the 4-position is carried out on the compound obtained in Step No. 3, accompanied or otherwise by a dehalogenation in the case of a 5-halogenated compound.

During the first step, the amine and alcohol functions of the 2-hydroxyalkylaniline, at the 1- and 2-positions of the benzene ring respectively, can be protected by any radical capable of protecting an amine function or an alcohol function such as, for example, an alkylcarbonyl, alkylsulfonyl or phenylsulfonyl radical.

The method of synthesis of the invention can be summarized according to the following general synthesis scheme:

GENERAL SYNTHESIS SCHEME

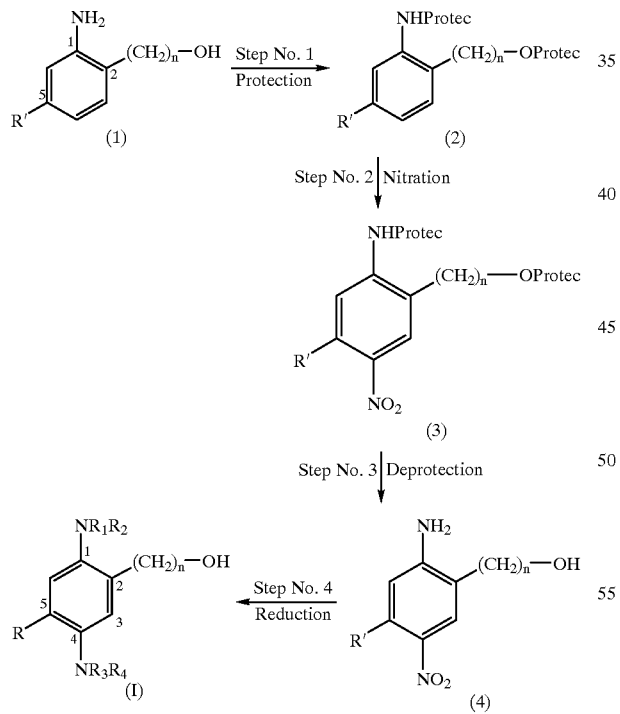

in which:
n is an integer from 1 to 4 inclusive;
Protec means a protecting group for the amine function and for the alcohol function;
R' represents a halogen atom such as bromine, chlorine or fluorine, or a $C_1$–$C_6$ alkyl radical;

R represents a hydrogen atom or has the same meanings as R';

$R_1$, $R_2$, $R_3$ and $R_4$, which are identical or different, designate a hydrogen atom, a radical: $C_1$–$C_6$ alkyl, $C_1$–$C_6$ monohydroxyalkyl, $C_2$–$C_6$ polyhydroxyalkyl, $C_1$–$C_6$ alkoxy-$C_1$–$C_6$ alkyl, $C_1$–$C_6$ aminoalkyl, mono- or dihydroxy($C_1$–$C_6$ alkyl)amino($C_1$–$C_6$ alkyl); ($C_1$–$C_6$ mono- or dialkyl)amino($C_1$–$C_6$ alkyl); aminoalkyl whose amine is protected with a ($C_1$–$C_6$ alkyl) carbonyl, carbamyl or ($C_1$–$C_6$ alkyl)sulfonyl radical; $C_1$–$C_6$ carboxyalkyl; $C_1$–$C_6$ cyanoalkyl; $C_1$–$C_6$ amidoalkyl; $C_1$–$C_6$ trifluoroalkyl; $C_1$–$C_6$ sulfonamidoalkyl; ($C_1$–$C_6$ alkyl)carboxy($C_1$–$C_6$ alkyl); ($C_1$–$C_6$ alkyl)sulfoxy($C_1$–$C_6$ alkyl); ($C_1$–$C_6$ alkyl)sulfone ($C_1$–$C_6$ alkyl); ($C_1$–$C_6$ alkyl)keto($C_1$–$C_6$ alkyl); ($C_1$–$C_6$ N-alkyl)amido($C_1$–$C_6$ alkyl) or ($C_1$–$C_6$ N-alkyl)sulfonamido($C_1$–$C_6$ alkyl);

it being understood that at least one of the groups —$NR_1R_2$ and —$NR_3R_4$ designates an —$NH_2$ group.

According to the invention, the alkyl radicals may be linear or branched.

The method of synthesis in accordance with the invention is essentially distinguishable from that of the prior art by the fact that the starting compound is a 2-hydroxyalkylaniline comprising a substituent at the 5-position of the benzene ring, which has the effect of orienting the nitration reaction to the 4-position of the benzene ring and, consequently, of considerably increasing the yield of the intermediate nitration reaction (Step No. 2).

By way of comparison, the applicant, in parallel with the prior art method of synthesis described above for the compounds in which n=2, carried out the synthesis of 2-β-hydroxyethyl-para-phenylenediamine with a good overall yield from 5-chloro-2-β-hydroxyethylaniline. The yield obtained after carrying out Steps 2 and 3 as described above for the general method of synthesis in accordance with the invention was 86.4%, instead of 8% for the prior art method of synthesis.

The 2-hydroxyalkyl-para-phenylenediamines which are substituted or unsubstituted at the 5-position on the benzene ring, as well as their addition salts with an acid which can be obtained according to the method in accordance with the invention, preferably correspond to the following formula (I):

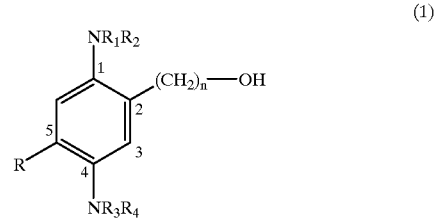

in which:
n is an integer from 1 to 4 inclusive;
R designates a hydrogen atom or a halogen atom such as bromine, chlorine or fluorine, a $C_1$–$C_6$ alkyl radical or a group OZ or SZ in which Z designates a $C_1$–$C_6$ alkyl, $C_1$–$C_6$ monohydroxyalkyl or $C_2$–$C_6$ polyhydroxyalkyl radical; $R_1$, $R_2$, $R_3$ and $R_4$, which are identical or different, designate a hydrogen atom, a radical: $C_1$–$C_6$ alkyl, $C_1$–$C_6$ monohydroxyalkyl, $C_2$–$C_6$ polyhydroxyalkyl, $C_1$–$C_6$ alkoxy-$C_1$–$C_6$ alkyl, $C_1$–$C_6$ aminoalkyl, mono- or dihydroxy($C_1$–$C_6$ alkyl)amino ($C_1$–$C_6$ alkyl); ($C_1$–$C_6$ mono- or dialkyl)amino($C_1$–$C_6$ alkyl); aminoalkyl whose amine is protected with a ($C_1$–$C_6$ alkyl)carbonyl, carbamyl or ($C_1$–$C_6$ alkyl)sulfonyl radical; $C_1$–$C_6$ carboxyalkyl; $C_1$–$C_6$ cyanoalkyl; $C_1$–$C_6$ amidoalkyl; $C_1$–$C_6$ trifluoroalkyl; Cl-$C_6$ sulfonamidoalkyl; ($C_1$–$C_6$ alkyl)carboxy ($C_1$—$C_6$ alkyl); ($C_{1-C6}$ alkyl)sulfoxy($C_1$–$C_6$ alkyl); ($C_1$–$C_6$ alkyl)sulfone(Cl-$C_6$ alkyl); ($C_1$–$C_6$ alkyl)keto (Cl-$C_6$ alkyl); (Cl-$C_6$ N-alkyl)amido($C_1$–$C_6$ alkyl) or ($C_1$–$C_6$ N-alkyl)sulfonamido($C_1$–$C_6$ alkyl);

it being understood that at least one of the groups —$NR_1R_2$ and —$NR_3R_4$ designates an —$NH_2$ group.

According to a first embodiment of the method of synthesis in accordance with the invention, the particular compounds of the following formula (Ia) and their addition salts with an acid:

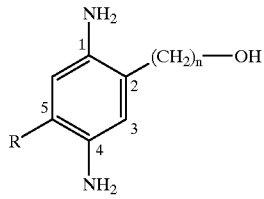

(Ia)

in which the radicals $R_1$, $R_2$, $R_3$ and $R_4$ simultaneously designate a hydrogen atom and R and n have the same meanings as those indicated above for formula (I), can be prepared according to the method of synthesis A comprising, in a first step, in carrying out, on a compound of the following formula (1):

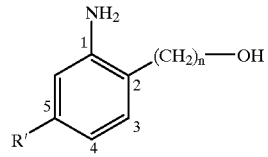

(1)

in which R' designates a halogen atom or a $C_1$–$C_6$ alkyl radical and n has the same meaning as that indicated above for formula (I), an acetylation reaction in order to obtain a compound of the following formula (2):

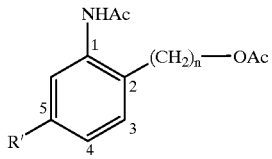

(2)

in which R' and n have the same meanings as those indicated above for formula (1) and Ac represents an acetyl group, and then in a second step, in carrying out, on the compound of formula (2) thus obtained, a reaction of nitration at the 4-position of the benzene ring, in order to obtain a compound of the following formula (3):

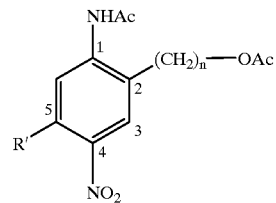

(3)

in which R', n and Ac have the same meanings as those indicated above for formula (2), and then in a third step, in carrying out, on the compound of formula (3), a deacetylation reaction in order to obtain the compound of the following formula (4):

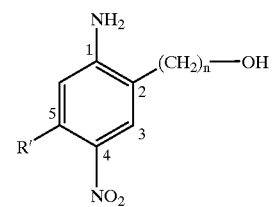

(4)

in which R' and n have the same meanings as those indicated above for formula (3), and then in order to obtain the compounds of formula (I) in which R designates a group OZ or SZ, a compound of formula (4), in which R' designates a halogen atom, is reacted, in a step 3', with an alcohol of formula HOZ or a thiol of formula HSZ in which Z has the same meanings as those indicated for formula (I) in order to obtain a compound of the following formula (4'):

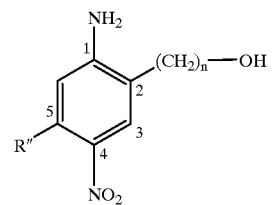

(4')

in which R" designates a group OZ or SZ, Z and n having the same meanings as those indicated for the formula (I) above, and then in a fourth step, a reduction reaction is carried out on the compound of formula (4) or (4'), it being understood that when the compound of formula (4), in which R' designates a halogen atom, is caused to react, the mode of reduction is chosen from the following methods:

in order to obtain the compounds of formula (Ia) in which R designates a hydrogen atom, a dehalogenating reduction reaction is carried out;

in order to obtain the compounds of formula (Ia) in which R designates a halogen atom, a non-dehalogenating reduction reaction is carried out.

According to a variant of this method of synthesis A in accordance with the invention, it is also possible to react, in a step 2', a compound of formula (3), in which R' designates a halogen atom, with an alcohol of formula HOZ or a thiol of formula HSZ, Z having the same meanings as those indicated for the formula (1), in order to obtain a compound of the following formula (3'):

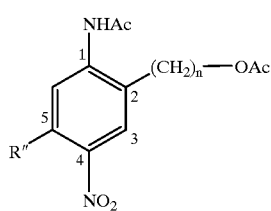

in which Ac and R" have the same meanings as those indicated above for the formula (4'), and then carry out deacetylation reaction in order to obtain the compound of formula (4') as defined above.

The method of synthesis A of the particular compounds of formula (Ia) can be represented by the following scheme A:

According to a second embodiment of the method of synthesis in accordance with the invention, the particular compounds of the following formula (Ib) and their addition salts with an acid:

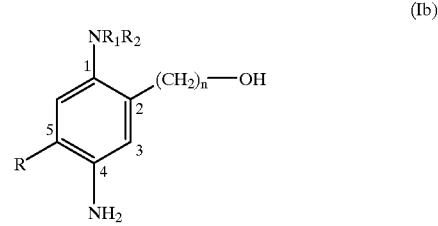

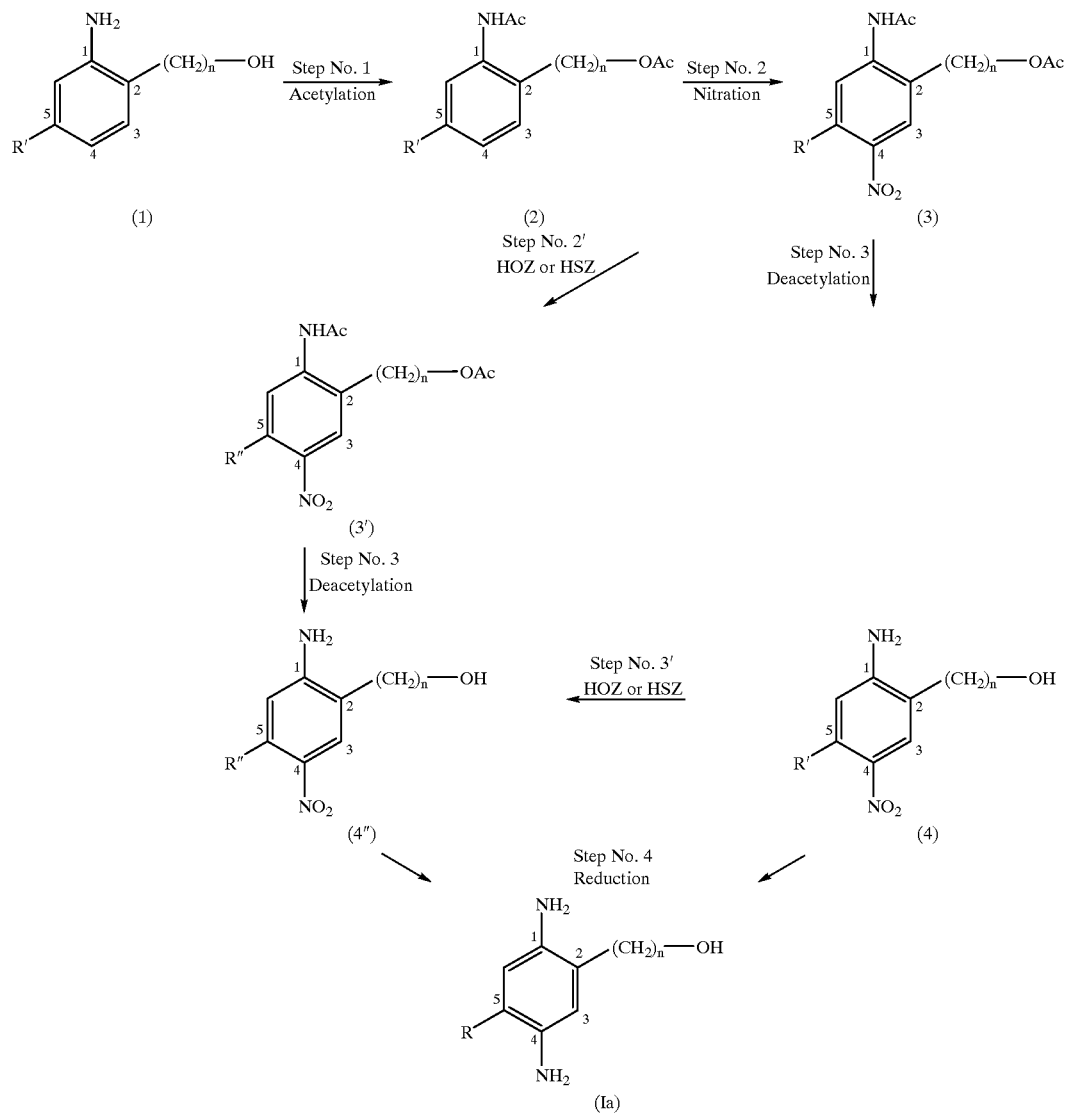

in which:

R₁, R₂, R and n have the same meanings as those indicated above for formula (I), it being understood that at least one of the radicals R₁ and R₂ is different from a hydrogen atom, can be prepared according to the method of synthesis B comprising carrying out steps 1, 2 and 3 of the method of synthesis A described above in order to obtain a compound of formula (4) as described above, and then in a step 3", in carrying out on said compound of formula (4) the substitution of the amine function at the 1-position of the benzene ring with the radicals R₁ and/or R₂, in order to obtain a compound of the following formula (5):

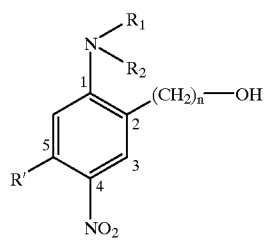

(5)

in which R' and n have the same meanings as those indicated above for formula (3) and R₁ and R₂ have the same meanings as those indicated above for formula (Ib), and then in order to obtain the compounds of formula (I) in which R designates a group OZ or SZ, a compound of formula (5), in which R' designates a halogen atom, is reacted in a step 3' with an alcohol of formula HOZ or a thiol of formula HSZ in which Z has the same meaning as that indicated for formula (I), in order to obtain a compound of the following formula (5'):

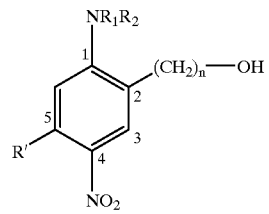

(5')

in which R" designates a group OZ or SZ, Z and n having the same meanings as those indicated in the formula (I) above, and then in a fourth step, a reduction reaction is carried out on the compound of formula (5) or (5'), it being understood that when a compound of formula (5), in which R' designates a halogen atom, is caused to react, the mode of reduction is chosen from the following methods:

in order to obtain the compounds of formula (Ib) in which R designates a hydrogen atom, a dehalogenating reduction reaction is carried out;

in order to obtain the compounds of formula (Ib) in which R designates a halogen atom, a non-dehalogenating reduction reaction is carried out.

This method of synthesis B may be represented by the following scheme B.

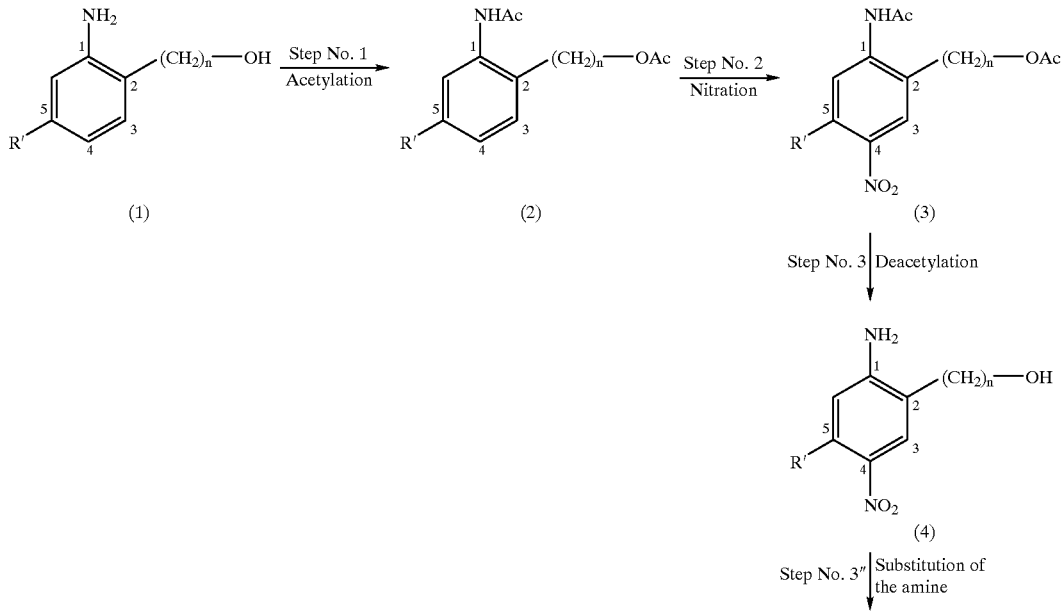

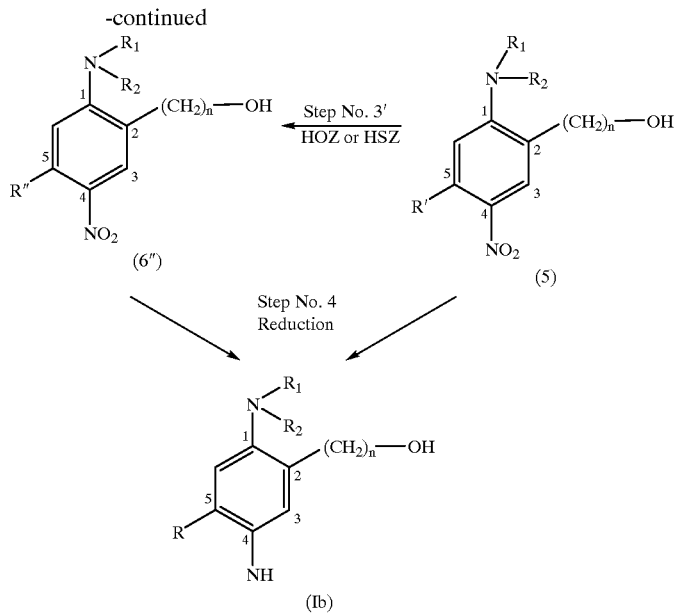

According to a particular variant of the method of synthesis B of the compounds of formula (Ib) presented above, the substitution of the radical R' designating a halogen atom with a radical R" designating OZ or SZ (step 3') may take place before the step 3" of substitution of the amine at the 1-position. It is also possible to react, in a step (2'), a compound of formula (3), in which R' designates a halogen atom, with an alcohol of formula HOZ or a thiol of formula HSZ, Z having the same meanings as those indicated for formula (1), in order to obtain a compound of formula (3') as defined above, and then carry out a deacetylation reaction in order to obtain a compound of formula (4') as defined above, followed by the substitution of the amine function at the 1-position of the benzene ring with a radical $R_1$ and/or $R_2$, in order to obtain a compound of formula (5').

This particular variant of the method of synthesis B may be represented by the synthesis scheme B' below:

SCHEME B'

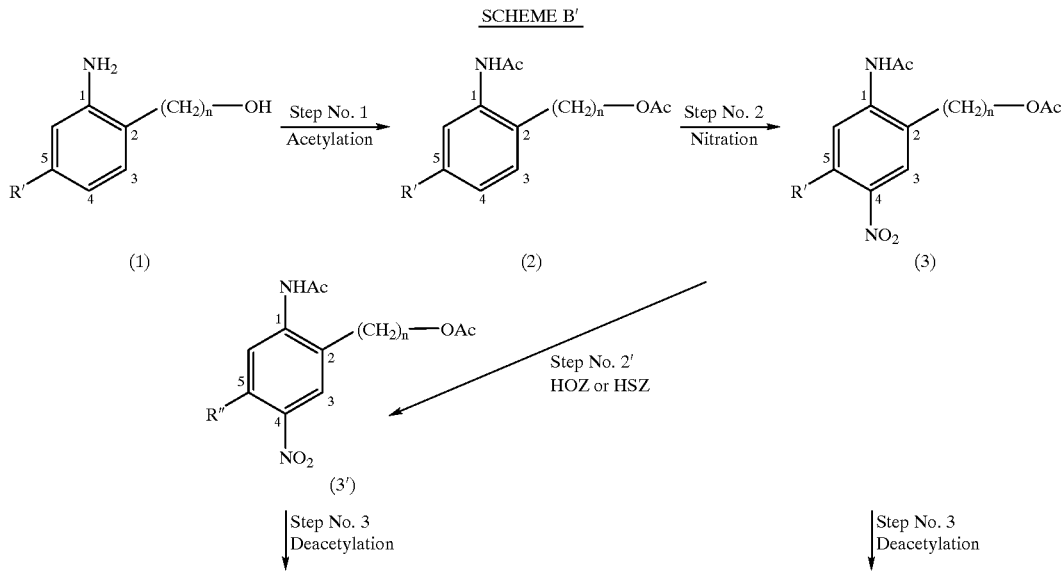

-continued

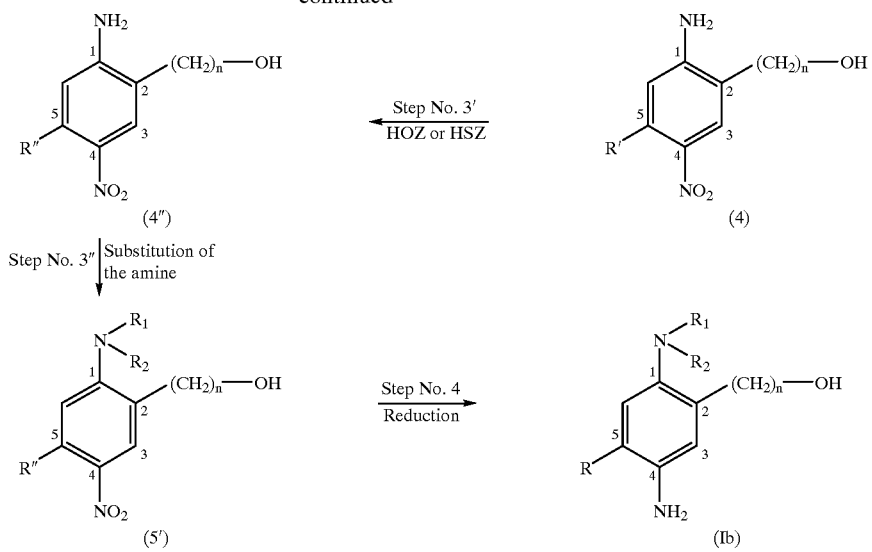

According to a third embodiment of the method of synthesis in accordance with the invention, the particular compounds of the following formula (Ic) and their addition salts with an acid:

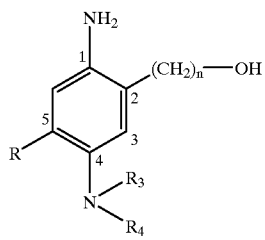

(Ic)

in which $R_1$, $R_3$, $R_4$ and n have the same meanings as those indicated for formula (I) above, it being understood that at least one of the radicals $R_3$ and $R_4$ is different from a hydrogen atom, can be prepared according to the method of synthesis C comprising in carrying out steps 1 and 2 of the method of synthesis A described above in order to obtain a compound of formula (3) as described above, and then in order to obtain the compounds of formula (Ic) in which R designates a group OZ or SZ, in reacting, in a step 3', a compound of formula (3), in which R' designates a halogen atom, with an alcohol of formula HOZ or a thiol of formula HSZ in which Z has the same meanings as those indicated for formula (1), in order to obtain a compound of the following formula

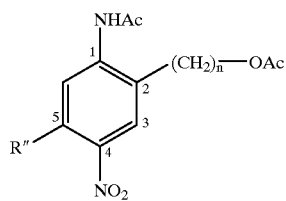

(3')

in which R" and Ac have the same meanings as those indicated above, and then in a fourth step, in carrying out a reduction reaction on the compound of formula (3) or (3'), it being understood that when the compound of formula (3), in which R' designates a halogen atom, is caused to react, the mode of reduction is chosen from the following methods:
  in order to obtain the compounds of formula (Ic) in which R designates a hydrogen atom, a dehalogenating reduction reaction is carried out;
  in order to obtain the compounds of formula (Ic) in which R designates a halogen atom, a non-dehalogenating reduction reaction is carried out; in order to obtain a compound of the following formula (6):

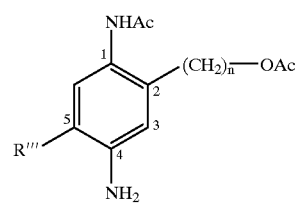

(6)

in which Ac has the same meaning as that indicated above and R'" represents a radical R' or R", R' and R" having the same meanings as those indicated above, and then in a fifth step, in carrying out on said compound of formula (6) the substitution of the amine function at the 4-position of the benzene ring with the radicals $R_3$ and/or $R_4$, in order to obtain a compound of the following formula (7):

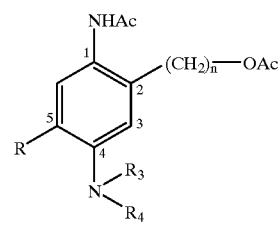

(7)

in which Ac, $R_3$, $R_4$, R and n have the same meanings as those indicated above, and then in a sixth step, in carrying out, on the compound of formula (7), a deacetylation reaction in order to obtain the compounds of formula (Ic) as described above.

This method of synthesis C may be represented by the following scheme C:
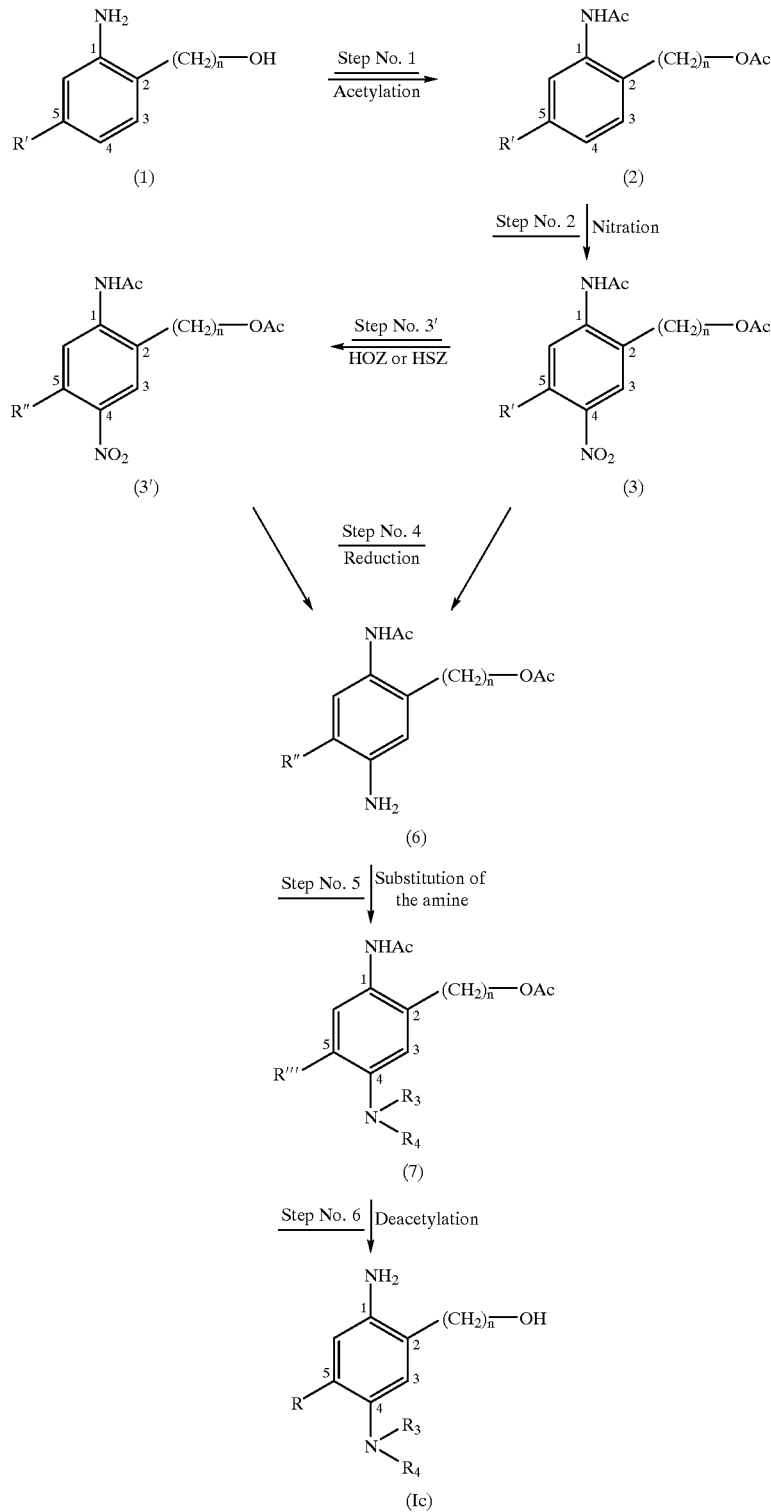

The acetylation reaction used during the first step of the general synthesis scheme (methods A, B, B' and C) can be carried out according to conventional methods of the state of the art such as, for example, at a temperature generally from 40 to 140° C. approximately, in the presence of acetic anhydride or of a mixture of acetic acid and acetic anhydride.

The nitration reaction used during the second step can be carried out according to conventional nitration methods known in the state of the art, preferably in sulfuric acid, at a temperature generally from −20 to +20° C., the nitrating agent being preferably nitric acid in sulfuric acid (sulfonitric mixture).

The deacetylation reaction used during the third step can be carried out according to the methods conventionally used in the literature, preferably in an acidic medium such as, for example, in the presence of hydrochloric acid, at a temperature generally from 20 to 100° C. approximately.

The reduction reaction used during the fourth step can be carried out by methods well known in the literature, preferably in alcohol, such as for example in ethanol, at a temperature generally from 20 to 100° C.

When it is desired to obtain a compound of formula (I) which is unsubstituted at the 5-position of the benzene ring (R=H), a dehalogenating reduction reaction can be carried out on a compound of formula (4) for the method of synthesis A, or on a compound of formula (5) for the method of synthesis B, or of formula (3) for the method of synthesis C, in which R' represents a halogen atom, by catalytic reduction in the presence of a catalyst such as for example palladium on carbon:

either under a hydrogen pressure generally from 1 to 50 bar;

or in the presence of a hydrogen donor such as for example cyclohexene, formic acid or ammonium formate.

When it is desired to obtain a compound of formula (I) which is substituted at the 5-position of the benzene ring with a halogen atom (R=halogen), a non-dehalogenating reduction can be carried out on a compound of formula (4) for the method of synthesis A, or on a compound of formula (5) for the method of synthesis B, or of formula (3) for the method of synthesis C, in which R' represents a halogen atom, for example by reduction in an iron/acetic medium or by reduction in a zinc/water/alcohol mixture.

When it is desired to obtain a compound of formula (I) in which R is different from a hydrogen or halogen atom, any mode of reduction conventionally used in the state of the art can be used.

All the reaction conditions described above are widely described in the literature, are only preferences and examples, and do not in any way limit the different operating conditions which can be used according to the method of synthesis in accordance with the invention.

Some 2-hydroxyalkyl-para-phenylenediamines of formula (I) defined above are new and constitute, as such, another subject of the invention.

These new 2-hydroxyalkyl-para-phenylenediamines and their addition salts with an acid correspond to the following formula (I'):

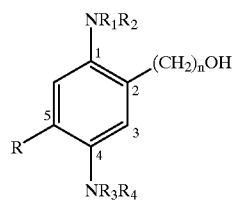

(I')

in which n, R, $R_1$, $R_2$, $R_3$ and $R_4$ have the same meanings as those indicated above for formula (I);

it being understood:

that at least one of the groups —$NR_1R_2$ and —$NR_3R_4$ designates an —$NH_2$ group; and that at least one of R, $R_1$, $R_2$, $R_3$ and $R_4$ is different from a hydrogen atom; and that when $R_1$, $R_2$, $R_3$ and $R_4$ simultaneously represent a hydrogen atom, and n is equal to 1, then R is not equal to hydrogen; or that when $R_1$ and $R_2$ simultaneously represent a hydrogen atom, n is equal to 1, and $R_3$ and $R_4$ represent β-hydroxyethyl groups, then R is not equal to hydrogen; or that when $R_1$ and $R_2$ simultaneously represent a hydrogen atom, n is equal to 1, $R_3$ represents an ethyl group, and $R_4$ represents methylcarboxyethyl, then R is not equal to a methyl group; or that when $R_1$, $R_2$, and $R_3$ simultaneously represent a hydrogen atom, n is equal to 1, and $R_4$ represents an amidomethyl group, then R is not equal to a methyl group; or that when $R_1$ and $R_2$ simultaneously represent a hydrogen atom, n is equal to 1, $R_3$ is methyl acetate, and $R_4$ represents an ethyl group, then R is not equal to a methyl group; or that when $R_1$ and $R_2$ simultaneously represent a hydrogen atom, n is equal to 1, $R_3$ and $R_4$ represent a methoxyethyl group, then R is not equal to a methyl group; or that when $R_1$, $R_2$, $R_3$ and $R_4$ simultaneously represent a hydrogen atom, and n is equal to 1, then R is not equal to a methyl group; or that when $R_1$, $R_2$, and $R_3$ simultaneously represent a hydrogen atom, n is equal to 1, and $R_4$ represents a hydroxyethyl group, then R is not equal to hydrogen; or that when $R_1$ and $R_2$ simultaneously represent a hydrogen atom, n is equal to 1, $R_3$ represents a methyl group and $R_4$ represents an n-butyl group, then R is not equal to a methyl group; or that when $R_1$, $R_2$, and $R_3$ simultaneously represent a hydrogen atom, n is equal to 1, and $R_4$ represents 2,3-hydroxypropyl, then R is not equal to hydrogen; or that when $R_1$, $R_2$, and $R_3$ simultaneously represent a hydrogen atom, n is equal to 1, and $R_4$ represents a methoxyethyl, then R is not equal to hydrogen; or that when $R_1$, $R_2$, and $R_3$ simultaneously represent a hydrogen atom, n is equal to 1, and $R_4$ represents methylcarboxyethyl, then R is not equal to a hydrogen atom; or that when $R_1$, $R_2$, and $R_3$ simultaneously represent a hydrogen atom, n is equal to 1, and $R_4$ represents n-pentyl, then R is not equal to a hydrogen atom; or that when $R_1$ and $R_2$ simultaneously represent a hydrogen atom, n is equal to 1, and $R_3$ and $R_4$ represent methyl or ethyl, then R is not equal to a hydrogen atom; or that when $R_1$ and $R_2$ simultaneously represent a hydrogen atom, n is equal to 1, $R_3$ represents an ethyl group and $R_4$ represents an n-butyl group, then R is not equal to hydrogen; or that when $R_1$ and $R_2$ simultaneously represent a hydrogen atom, n is equal to 1, and $R_3$ and $R_4$ represent methoxyethyl, then R is not equal to hydrogen; or that when $R_1$ and $R_2$ simultaneously represent a hydrogen atom, n is equal to 1, $R_3$ represents a β-hydroxy ethyl group and $R_4$ represents an amido methyl group, then R is not equal to hydrogen; or that when $R_1$ and $R_2$ simultaneously represent a hydrogen atom, n is equal to 1, $R_3$ represents an ethyl group and $R_4$ represents a carboxymethyl group, then R is not equal to hydrogen; or that when $R_1$ and $R_2$ simultaneously represent a hydrogen atom, n is equal to 1 or 2, and $R_3$ and $R_4$ represent an ethyl group, then R is not equal to hydrogen.

The provisos stated above were introduced in order to exclude from the invention compounds known in the state of the art, in particular in the photography field (U.S. Pat. No. 2,273 564; TONG L K J et al, Journal of The American Chemical Society, Vol. 82, No. 8, Apr. 25, 1960, pages 1988–1996; R. L. BENT, Journal of The American Chemical Society, Vol. 73, 1951, DC US, pages 3100–3125).

Among the 2-hydroxyalkyl-para-phenylenediamines of formula (I') above, there may be mentioned in particular:

2-(β-hydroxyethyl)-5-chloro-para-phenylenediamine,
2-(β-hydroxyethyl)-5-methoxy-para-phenylenediamine,
2-(β-hydroxyethyl)-5-methylthio-para-phenylenediamine,
2-(β-hydroxyethyl)-5-methyl-para-phenylenediamine,
4-amino-1-N-(β-hydroxyethyl)amino-2-(β-hydroxyethyl)benzene, and their addition salts with an acid.

The new 2-hydroxyalkyl-para-phenylenediamines of formula (I') in accordance with the invention can be used as an oxidation base in compositions for the oxidation dyeing of keratinous fibers and in particular human keratinous fibers such as hair, which constitutes another subject of the invention.

The subject of the invention is also the dyeing composition for dyeing keratinous fibers and in particular human keratinous fibers such as hair, characterized in that it contains, in an appropriate medium for dyeing, at least one 2-hydroxyalkyl-para-phenylenediamine of formula (I') as defined above, as oxidation base.

The 2-hydroxyalkyl-para-phenylenediamine(s) of formula (I') in accordance with the invention and/or the or their addition salts with an acid preferably represent(s) from 0.0005 to 12% by weight approximately of the total weight of the dyeing composition, and still more preferably from 0.005 to 6% by weight approximately of this weight.

The appropriate medium for dyeing (or carrier) generally comprises water or a mixture of water and at least one organic solvent for solubilizing the compounds which may be insufficiently soluble in water. As organic solvent, there may be mentioned for example the $C_1$–$C_4$ lower alkanols such as ethanol and isopropanol; glycerol; glycols or glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, analogous products and mixtures thereof.

The solvents may be present in proportions preferably of from about 1 to about 40% by weight relative to the total weight of the dyeing composition, and still more preferably from about 5 to about 30% by weight.

The pH of the dyeing composition in accordance with the invention is generally from approximately 3 to approximately 12, and preferably from approximately 5 to approximately 11. It may be adjusted to the desired value by means of acidifying or alkalinizing agents normally used in dyeing keratinous fibers.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, ammonium hydroxide, alkali metal carbonates, alkanolamines such as mono-, di- and triethanolamines as well as derivatives thereof, sodium or potassium hydroxides and the compounds of the following formula (II):

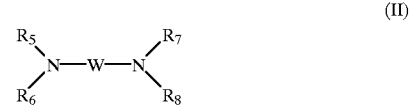

in which W is a propylene residue optionally substituted with a hydroxyl group or a $C_1$–$C_6$ alkyl radical; $R_5$, $R_6$, $R_7$, and $R_8$ which are identical or different, represent a hydrogen atom, a $C_1$–$C_6$ alkyl or $C_1$–$C_6$ hydroxyalkyl radical.

The dyeing composition in accordance with the invention may also contain, in addition to the 2-hydroxyalkyl-para-phenylenediamine of formula (I') defined above, at least one additional oxidation base which may be chosen from the oxidation bases conventionally used in oxidation dyeing and among which there may be mentioned in particular the para-phenylenediamines which are different from the compounds of formula (I') in accordance with the invention, the bis-phenylalkylenediamines, the para-aminophenols, the ortho-aminophenols and the heterocylic bases.

Among the para-phenylenediamines, there may be mentioned more particularly, by way of example, para-phenylenediamine, para-toluylenediamine, 2,6-dimethyl-para-phenylenediamine, 2-(β-hydroxyethyl)-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline, the para-phenylenediamines described in French patent application FR 2,630,438, and their addition salts with an acid.

Among the bis-phenylalkylenediamines, there may be mentioned more particularly, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-amino-phenyl)tetramethylenediamine, N,N'-bis(β-hydroxyethyl)-N,N'-bis(4-aminophenyl)tetramethylenediamine, N,N'-bis(4-methylaminophenyl)tetra-methylenediamine, N,N'-bis(ethyl)-N,N'-bis(4'-amino-3'-methylphenyl)ethylenediamine, and their addition salts with an acid.

Among the para-aminophenols, there may be mentioned more particularly, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

Among the ortho-aminophenols, there may be mentioned more particularly, by way of example, 2-aminophenol, 2-amino-5-methylphenol, 2-amino-6-methylphenol, 5-acetamido-2-aminophenol, and their addition salts with an acid.

Among the heterocyclic bases, there may be mentioned more particularly, by way of example, the pyridine derivatives, the pyrimidine derivatives and the pyrazole derivatives.

When they are used, these additional oxidation bases preferably represent from 0.0005 to 12% by weight approximately of the total weight of the dyeing composition, and still more preferably from 0.005 to 6% by weight approximately of this weight.

The oxidation dyeing compositions in accordance with the invention may also contain at least one coupler and/or at least one direct dye, especially to modify the shades or to enrich their shimmer.

The couplers which can be used in the oxidation dyeing compositions in accordance with the invention may be chosen from the couplers conventionally used in oxidation dyeing and among which there may be mentioned in particular meta-phenylenediamines, meta-aminophenols, meta-diphenols and heterocyclic couplers such as for example indole derivatives, indoline derivatives, pyridine derivatives and pyrazolones, and their addition salts with an acid.

These couplers are chosen especially from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-di-hydroxybenzene, 2,4-diamino-1-(β-hydroxyethyloxy)-benzene, 2-amino-4-(β-hydroxyethylamino)-1-methoxy-benzene, 1,3-diaminobenzene, 1,3-bis(2,4-diamino-phenoxy)propane, sesamol, a-naphthol, 6-hydroxyindole, 4-hydroxyindole, 4-hydroxy-N-methylindole, 6-hydroxy-indoline, 2,6-dihydroxy-4-methylpyridine, 1H-3-methylpyrazol-5-one, 1-phenyl-3-methylpyrazol-5-one, and their addition salts with an acid.

When they are present, these couplers preferably represent from 0.0001 to 10% by weight approximately of the total weight of the dyeing composition, and still more preferably from 0.005 to 5% by weight approximately of this weight.

In general, the addition salts with an acid which can be used within the framework of the dyeing compositions of the invention (compounds of formulae (I), (Ia), (Ib), (Ic), (I'), additional oxidation bases and couplers) are in particular chosen from hydrochlorides, hydrobromides, sulfates, citrates, succinates, tartrates, lactates and acetates.

The dyeing composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, antioxidants, penetrating agents, sequestering agents, perfumes, buffers, dispersing agents, conditioning agents such as for example modified or unmodified, volatile or nonvolatile silicones, film-forming agents, ceramides, preservatives and opacifying agents.

Of course, persons skilled in the art will take care to choose this or these possible additional compounds, such that the advantageous properties intrinsically attached to the oxidation dyeing composition in accordance with the invention are not, or are not substantially, altered by the addition (s) envisaged.

The dyeing composition in accordance with the invention may be provided in various forms, such as in the form of liquids, creams, gels or any other form appropriate for dyeing keratinous fibers and especially human hair. The subject of the invention is also a method of dyeing keratinous fibers, and in particular human keratinous fibers such as hair, using the dyeing composition as defined above.

According to this method, at least one dyeing composition as defined above is applied to the fibers, the color being developed at acidic, neutral or alkaline pH with the aid of an oxidizing agent which is added right at the time of use to the dyeing composition or which is present in an oxidizing composition applied simultaneously or sequentially in a separate manner.

According to a preferred embodiment of the dyeing method of the invention, the dyeing composition described above is preferably mixed, at the time of use, with an oxidizing composition containing, in an appropriate medium for dyeing, at least one oxidizing agent present in a sufficient quantity to develop a color. The mixture obtained is then applied to the keratinous fibers and left for approximately 3 to approximately 50 minutes preferably for approximately 5 to approximately 30 minutes, after which they are rinsed, washed with a shampoo, rinsed again and dried.

The oxidizing agent may be chosen from oxidizing agents conventionally used for the oxidation dyeing of keratinous fibers, and among which there may be mentioned hydrogen peroxide, urea peroxide, alkali metal bromates, persalts such as perborates and persulfates, peracids, enzymes such as peroxidases and oxidoreductases with 2 electrons. Hydrogen peroxide is particularly preferred.

The pH of the oxidizing composition containing the oxidizing agent as defined above is such that after mixing with the dyeing composition, the pH of the resulting composition applied to the keratinous fibers preferably varies from approximately 3 to approximately 12, and still more preferably from 5 to 11. It is adjusted to the desired value by means of acidifying or alkalinizing agents normally used in dyeing keratinous fibers and as defined above.

The oxidizing composition as defined above may also contain various adjuvants conventionally used in compositions for dyeing hair and as defined above.

The composition which is finally applied to the keratinous fibers may be provided in various forms, such as in the form of liquids, creams, gels, or any other form appropriate for dyeing keratinous fibers, and in particular human hair.

Another subject of the invention is a multicompartment device or multicompartment dyeing "kit" or any other multicompartment packaging system in which a first compartment contains the dyeing composition as defined above and a second compartment contains the oxidizing composition as defined above. These devices may be equipped with means which allow the desired mixture to be applied to the hair, such as the devices described in patent FR 2,586,913.

The examples which follow are intended to illustrate the invention without, however, limiting the scope thereof.

EXAMPLES

Example 1

Preparation of 5-chloro-2-(D-hydroxyethyl)-para-phenylenediamine dihydrochloride a) Synthesis of 2-(2-acetylamino-4-chloro-5-nitrophenyl) ethyl acetate A mixture of 76.0 g (0.442 mol) of 1-amino-5-chloro-2-(β-hydroxyethyl)benzene in 30 ml of acetic acid and 100 ml of acetic anhydride was prepared in a reactor. The reaction was exothermic. The mixture was heated on a boiling water bath, with stirring, for 2 hours until the intermediate N-[5-chloro-2-(β-hydroxyethyl)phenyl]acetamide disappeared (by thin-layer chromatography (TLC)).

After cooling on an ice bath (forming into a mass), the white crystals (73.6 g) of 2-(2-acetylamino-4-chlorophenyl) ethyl acetate melting at 129° C. (Kofler) were drained, washed with petroleum ether and dried under vacuum and over potassium hydroxide. 215 ml of 98% sulfuric acid were placed in a reactor and cooled to 0° C. The 73.6 g (0.287 mol) of the compound obtained above were added in portions, with stirring, while the temperature was kept at 0° C. (slow dissolution).

A solution of 20.6 ml of nitric acid (d=1.50) in 110 ml of 98% sulfuric acid was poured in dropwise, over 30 minutes and while the temperature was kept from −5° C. to 0° C.

The stirring was maintained for an additional 30 minutes from −5° C. to 0° C. and the reaction medium was poured into 1.6 kg of ice-cold water.

After having drained the precipitate, reformed into a paste several times in water and dried under vacuum at 40° C. over phosphoric anhydride, beige crystals (73.7 g) of 2-(2-acetylamino-4-chloro-5-nitrophenyl)ethyl acetate were obtained, melting at 153° C. (Kofler) and whose elemental analysis calculated for $C_{12}H_{13}N_2O_5Cl$ was:

| %          | C     | H    | N    | O     | Cl    |
|------------|-------|------|------|-------|-------|
| Calculated | 47.93 | 4.36 | 9.32 | 26.60 | 11.79 |
| Found      | 47.96 | 4.39 | 9.15 | 26.61 | 11.64 | b) Synthesis of 1-amino-5-chloro-2-(β-hydroxyethyl)-4-nitrobenzene 19.7 g (0.065 mol) of the product obtained above in the preceding step were deacetylated in 60 ml of 36% hydrochloric acid heated on a boiling water bath for 45 minutes.

The reaction medium was poured over 200 g of ice-cold water, made basic by addition of 10 N caustic soda, the precipitate drained, reformed into a paste in water and dried under vacuum at 40° C. over phosphoric anhydride.

13.6 g of light-yellow crystals of 1-amino-5-chloro-2-(β-hydroxyethyl)-4-nitrobenzene were obtained, melting at 176° C. (Kofler) and whose elemental analysis calculated for $C_8H_9N_2O_3Cl$ was:

| %          | C     | H    | N     | O     | Cl    |
|------------|-------|------|-------|-------|-------|
| Calculated | 44.36 | 4.19 | 12.93 | 22.16 | 16.37 |
| Found      | 44.44 | 4.23 | 12.87 | 22.01 | 16.13 | c) Reduction of the 1-amino-5-chloro-2-(β-hydroxyethyl)-4-nitrobenzene

A suspension of 0.4 g of ammonium chloride and 15 g of fine zinc powder in 4 ml of water and 23 ml of 96% ethanol was heated at the reflux temperature of alcohol.

5.1 g (0.0235 mol) of the nitro derivative obtained above in the preceding step were added in portions so as to maintain the reflux without heating (the reaction being exothermic). At the end of the addition, the reflux was maintained for an additional 10 minutes, the mixture was filtered while boiling hot over 15 ml of approximately 6 N ice-cold hydrochloric ethanol and the zinc slurry was washed with boiling absolute ethanol.

The filtrate was cooled on an ice-bath and the precipitate drained and washed with ethyl ether.

After drying at 40° C. under vacuum and over potassium hydroxide, white crystals of 5-chloro-2-(β-hydroxyethyl)-para-phenylenediamine dihydrochloride were obtained, melting with decomposition at 192°–194° C. (Kofler) and whose elemental analysis calculated for $C_8H_{11}N_2OCl.2HCl$ was:

| %          | C     | H    | N     | O    | Cl    |
|------------|-------|------|-------|------|-------|
| Calculated | 37.02 | 5.05 | 10.79 | 6.16 | 40.98 |
| Found      | 37.03 | 5.09 | 10.9  | 6.77 | 40.44 |

Example 2

Preparation of 2-(β-hydroxyethyl)-5-methoxy-para-phenylenediamine, dihydrochloride, ¼ $H_2O$ a) Synthesis of 1-amino-2-(β-hydroxyethyl)-5-methoxy-4-nitrobenzene The mixture of 21.6g (0.1 mol) of 1-amino-5-chloro-2-(β-hydroxyethyl)-4-nitrobenzene obtained above in Example 1, step b), 50 ml of methanol and 40 ml of a 30% solution of sodium methoxide in methanol was heated for 4 hours under reflux.

The mixture was poured over 500 ml of ice-cold water, the crystallized precipitate drained, reformed into a paste in water and dried under vacuum at 40° C. over phosphoric anhydride.

Yellow crystals (15.8 g) were obtained which, after purification by recrystallization from boiling ethanol, melted at 145° C. (Kofler) and whose elemental analysis calculated for $C_9H_{12}N_2O_4$ was:

| %          | C     | H    | N     | O     |
|------------|-------|------|-------|-------|
| Calculated | 50.94 | 5.70 | 13.20 | 30.16 |
| Found      | 50.85 | 5.7t | 13.16 | 30.22 | b) Reduction of the 1-amino-2-(β-hydroxyethyl)-5-methoxy-4-nitrobenzene

The procedure described for Example 1, step c) was used.

By reducing 10.0 g (0.047 mol) of 1-amino-2-(β-hydroxyethyl)-5-methoxy-4-nitrobenzene obtained in the preceding step, 10.7 g of white crystals of 2-(β-hydroxyethyl)-5-methoxy-para-phenylene diamine (crystallized with ¼ $H_2O$) melting with decomposition at 216–218° C. (Kofler) were obtained and whose elemental analysis calculated for $C_9H_{14}N_2O_2 \cdot 2HCl + ¼ H_2O$ was:

| %          | C     | H    | N     | O     | Cl    |
|------------|-------|------|-------|-------|-------|
| Calculated | 41.63 | 6.41 | 10.79 | 13.86 | 27.31 |
| Found      | 41.58 | 6.57 | 10.70 | 14.50 | 27.31 |

Example 3

Preparation of 2-(β-hydroxyethyl)-5-methylthio-para-phenylenediamine, dihydrochloride a) Synthesis of 1-amino-2-((β-hydroxyethyl)-5-methylthio-4-nitrobenzene A suspension of 9.5 g of sodium thiomethoxide was prepared in 100 ml of 1,2-dimethoxyethane and with stirring 21.6 g (0.1 mol) of 1-amino-5-chloro-2-(β-hydroxyethyl)-4-nitrobenzene obtained above in Example 1, step b) were added.

The mixture was heated for 30 minutes at 50° C. and then for 10 minutes at 65° C.

The mixture was poured over 800 ml of ice-cold water, the crystallized precipitate drained, reformed into a paste in water and dried under vacuum at 40° C. over phosphoric anhydride.

Yellow crystals (21.0 g) were obtained which, after purification by recrystallization from boiling ethyl acetate, melted at 180° C. (Kofler) and whose elemental analysis calculated for $C_9H_{12}N_2O_3S$ was:

| %          | C     | H    | N     | O     | S     |
|------------|-------|------|-------|-------|-------|
| Calculated | 47.36 | 5.30 | 12.27 | 21.03 | 14.05 |
| Found      | 47.92 | 5.27 | 12.05 | 21.49 | 13.38 | b) Reduction of the 1-amino-2-(β-hydroxyethyl)-5-methylthio-4-nitrobenzene

The procedure described above for Example 1, step c) was used.

By reducing 15.5 g (0.068 mol) of 1-amino-2-(β-hydroxyethyl)-5-methylthio-4-nitrobenzene obtained above in step a), 16.8 g of white crystals of 2-((β-hydroxyethyl)-5-methylthio-para-phenylenediamine were obtained melting with decomposition at 182–184° C. (Kofler) and whose $^1H$ NMR analysis was in conformity with that of the expected product.

Example 4

Preparation of 2-(β-hydroxyethyl)-5-methyl-para-phenylenediamine, dihydrochloride a) Synthesis of 2-(2-acetylamino-4-methyl-5-nitrophenyl) ethyl acetate The procedure described above for Example 1, step a) was used.

Starting with 23.5 g (0.155 mol) of 1-amino-2-(β-hydroxyethyl)-5-methylbenzene, cream-colored crystals (19.2 g) of 2-(2-acetylamino-4-methyl-5-nitrophenyl)ethyl acetate were obtained which, after purification by recrystallization from boiling ethyl acetate, melted at 125° C. (Kofler) and whose elemental analysis calculated for $C_{13}H_{16}N_2O_5 \cdot \frac{1}{2}H_2O$ was:

| %          | C     | H    | N    | O     |
|------------|-------|------|------|-------|
| Calculated | 53.98 | 5.92 | 9.68 | 30.42 |
| Found      | 54.24 | 5.68 | 9.70 | 30.42 | b) Deacetylation—reduction of the 2-(2-acetylamino-4-methyl-5-nitrophenyl)ethyl acetate By deacetylation (according to the procedure described above for step b) of Example 1), of 19.0 g (0.067 mol) of the compound obtained above in the preceding step, 7.5 g of pale-yellow crystals of 1-amino-2-(β-hydroxyethyl)-5-methyl-4-nitrobenzene were obtained, after purification by recrystallization from ethanol, whose melting point (Kofler) was 168° C.

The reduction according to the procedure described above for Example 1, step c) of these 7.5 g (0.038 mol) of 1-amino-2-(β-hydroxyethyl)-5-methyl-4-nitrobenzene gave white crystals (7.5 g) of 2-(β-hydroxyethyl)-5-methyl-para-phenylenediamine dihydrochloride melting with decomposition at 208–210° C. (Kofler) and whose elemental analysis calculated for $C_9H_{16}N_2OCl_2$ was:

| %          | C     | H    | N     | O    | Cl    |
|------------|-------|------|-------|------|-------|
| Calculated | 45.20 | 6.74 | 11.71 | 6.69 | 29.65 |
| Found      | 45.11 | 6.77 | 11.65 | 7.09 | 29.47 |

Example 5

Preparation of 4-amino-2-(β-hydroxyethyl)-1-N-(β-hydroxyethyl)aminobenzene, dihydrochloride a) Synthesis of 5-chloro-1-N-(β-hydroxyethyl)amino-2-(β-hydroxyethyl)-4-nitrobenzene The mixture of 10.8g (0.05 mol) of 1-amino-5-chloro-2-(β-hydroxyethyl)-4-nitrobenzene obtained above in Example 1, step b), and 5.5 g (0.055 mol) of calcium carbonate in 50 ml of dioxane was heated on a boiling water bath.

5.7 ml (0.055 mol) of β-chloroethylchloroformate were added dropwise and the heating was continued for one hour.

The mixture was poured over 300 ml of ice-cold water, acidified with hydrochloric acid, the crystallized white precipitate drained, reformed into a paste in water and suspended in 27 ml of water.

18 ml of 10 N caustic soda were added and the mixture was heated at 65° C. for one hour, with stirring.

An oil separated after settling out and crystallized. The product was drained, reformed into a paste in water and dried under vacuum.

Yellow crystals (10.9 g) were obtained which, after purification by recrystallization from boiling ethanol, melted at 129° C. (Kofler) and whose elemental analysis calculated for $C_{10}H_{13}N_2O_4Cl$ was:

| %          | C     | H    | N     | O     | Cl    |
|------------|-------|------|-------|-------|-------|
| Calculated | 46.08 | 5.03 | 24.55 | 10.75 | 13.60 |
| Found      | 45.78 | 5.02 | 24.46 | 10.63 | 13.42 | b) Dehalogenating reduction of 5-chloro-1-N-(β-hydroxyethyl)amino-2-(β-hydroxyethyl)-4-nitrobenzene A mixture of 8.0 g (0.0306 mol) of 5-chloro-1-N-(β-hydroxyethyl)amino-2-(β-hydroxyethyl)-4-nitrobenzene obtained above in the preceding step and 9.0 g of 5% palladium on carbon and containing 50% water in 30 ml of ethanol was heated under reflux.

25 ml of cyclohexane were added dropwise and the mixture was heated under reflux, with stirring, for 3 hours.

The mixture was filtered while boiling hot and the filtrate poured into 30 ml of 5 N hydrochloric absolute ethanol. After evaporation to dryness under reduced pressure and trituration of the gum obtained in a mixture of absolute ethanol and ethyl ether, 5.3 g of hygroscopic white crystals of 4-amino-2-(β-hydroxyethyl-1-N-(β-hydroxyethyl) aminobenzene dihydrochloride were obtained melting with decomposition at 120–122° C. (Kofler) and whose $^1H$ NMR structure for the product obtained was in conformity with that of the expected product.

Examples 6 to 11 of Dyes

The following dye compositions were prepared (amounts in grams):

| EXAMPLE | 6 | 7 | 8 | 9 | 10 | 11 |
|---|---|---|---|---|---|---|
| 5-Chloro-2-(β-hydroxyethyl)-para-phenylenediamine dihydrochloride (oxidation base) | 0.779 | — | — | — | — | — |
| 5-Methoxy-2-(β-hydroxyethyl)-para-phenylenediamine dihydrochloride (oxidation base) | — | 0.765 | 0.765 | — | — | — |
| 5-Methylthio-2-(β-hydroxyethyl)-para-phenylenediamine dihydrochloride (oxidation base) | — | — | — | 0.814 | — | — |
| 5-Methyl-2-(β-hydroxyethyl)-para-phenylenediamine dihydrochloride (oxidation base) | — | — | — | — | 0.717 | — |
| 4-Amino-1-N-(β-hydroxyethyl)amino-2-(β-hydroxyethyl)benzene dihydrochloride (oxidation base) | — | — | — | — | — | 0.807 |
| 2,4-Diaminophenoxyethanol dihydrochloride (coupler) | 0.722 | — | — | 0.722 | 0.722 | — |
| Meta-aminophenol (coupler) | — | 0.327 | — | — | — | — |
| 6-Hydroxyindol (coupler) | — | — | 0.4 | — | — | — |
| ethyl)aminophenol (coupler) | | | | | | |
| 2-Methyl-5-N-(β-hydroxy- | — | — | — | — | — | 0.5 |
| Common dye carrier | (*) | (*) | (*) | (*) | (*) | (*) |
| Demineralized water qs | 100 g | 100 g | 100 g | 100 g | 100 g | 100 g |

(*) common dye carrier:

| | | |
|---|---|---|
| Polyglycerolated oleyl alcohol containing 2 moles of glycerol | 4.0 | g |
| Polyglycerolated oleyl alcohol containing 4 moles of glycerol, containing 78% active materials (A.M.) | 5.69 | gA.M. |
| Oleic acid | 3.0 | g |
| Oleylamine containing 2 moles of ethylene oxide sold under the tradename ETHOMEEN 012 by the company AKZO | 7.0 | g |
| Diethylaminopropyl laurylaminosuccinamate, sodium salt, containing 55% of A.M. | 3.0 | gA.M. |
| Oleyl alcohol | 5.0 | g |
| Oleic acid diethanolamide | 12.0 | g |
| Propylene glycol | 3.5 | g |
| Ethyl alcohol | 7.0 | g |
| Dipropylene glycol | 0.5 | g |
| Propylene glycol monomethyl ether | 9.0 | g |
| Sodium metabisulfite in aqueous solution containing 35% A.M. | 0.455 | gA.M. |
| Ammonium acetate | 0.8 | g |
| Antioxidant, sequestrant | qs | |
| Perfume, preservative | qs | |
| Aqueous ammonia containing 20% NH₃ | 10.0 | g |

At the time of use, each dyeing composition above was mixed with an equivalent quantity by weight of an oxidizing composition comprising of a solution of hydrogen peroxide at 20 volumes (6% by weight).

Each resultant composition was applied for 30 minutes to locks of natural grey hair which was 90% white. The hair locks were then rinsed, washed with a standard shampoo and then dried.

The shades obtained are presented in the table below:

| EXAMPLE | DYEING pH | SHADE OBTAINED |
|---|---|---|
| 6 | 10 (0.2 | very light bluish ash blonde |
| 7 | 10 (0.2 | very blue ash blonde |
| 8 | 10 (0.2 | mahogany beige blonde |
| 9 | 10 (0.2 | light bluish ash blonde |
| 10 | 10 (0.2 | blue ash blonde |
| 11 | 10 (0.2 | pale deep purple ash blonde |

We claim:

1. A 2-Hydroxyalkyl-para-phenylenediamine of the formula (I'), or an acid addition salt thereof:

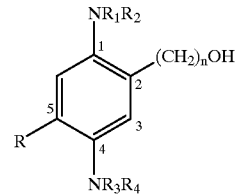

(I')

in which:

n is an integer from 1 to 4 inclusive;

$R_1$, $R_2$, $R_3$ and $R_4$, which are identical or different, are selected from a hydrogen atom and the following radicals:

$C_1$–$C_6$ alkyl,
$C_1$–$C_6$ monohydroxyalkyl,
$C_2$–$C_6$ polyhydroxyalkyl,
$C_1$–$C_6$ alkoxy-$C_1$–$C_6$ alkyl,
$C_1$–$C_6$ aminoalkyl,
mono- or dihydroxy($C_1$–$C_6$ alkyl)amino($C_1$–$C_6$ alkyl),
($C_1$–$C_6$ mono- or dialkyl)amino($C_1$–$C_6$ alkyl),
aminoalkyl whose amine is protected with a ($C_1$–$C_6$ alkyl) carbonyl, carbamyl or ($C_1$–$C_6$ alkyl)sulfonyl radical,
$C_1$–$C_6$ carboxyalkyl,
$C_1$–$C_6$ cyanoalkyl,
$C_1$–$C_6$ amidoalkyl,
$C_1$–$C_6$ trifluoroalkyl,
$C_1$–$C_6$ sulfonamidoalkyl,
($C_1$–$C_6$ alkyl)carboxy($C_1$–$C_6$ alkyl),
($C_1$–$C_6$ alkyl)sulfoxy($C_1$–$C_6$ alkyl),
($C_1$–$C_6$ alkyl)sulfone($C_1$–$C_6$ alkyl),
($C_1$–$C_6$ alkyl)keto($C_1$–$C_6$ alkyl),
($C_1$–$C_6$ N-alkyl)amido($C_1$–$C_6$ alkyl) and
($C_1$–$C_6$ N-alkyl)sulfonamido($C_1$–$C_6$ alkyl);

R designates a hydrogen atom, a halogen atom, a $C_1$–$C_6$ alkyl radical or a group OZ or SZ in which Z designates a $C_1$–$C_6$ alkyl, $C_1$–$C_6$ monohydroxyalkyl or $C_2$–$C_6$ polyhydroxyalkyl nradical;

it being understood that at least one of the groups —$NR_1R_2$ and —$NR_3R_4$ designates an —$NH_2$ group; and that at least one of R, $R_1$, $R_2$, $R_3$ and $R_4$ is different from a hydrogen atom; and that when $R_1$ and $R_2$ simultaneously represent a hydrogen atom, n is equal to 1, $R_3$ represents an ethyl group, and $R_4$ represents methylcarboxyethyl, then R is not equal to a methyl group; or that when $R_1$, $R_2$, and $R_3$ simultaneously represent a hydrogen atom, n is equal to 1, and $R_4$ represents an amidomethyl group, then R is not equal to a methyl group; or that when $R_1$ and $R_2$ simultaneously represent a hydrogen atom, n is equal to 1, $R_3$ is methyl acetate, and $R_4$ represents an ethyl group, then R is not equal to a methyl group; or that when $R_1$, $R_2$, and $R_3$ simultaneously represent a hydrogen atom, n is equal to 1, and $R_4$ represents methylcarboxyethyl, then R is not equal to a hydrogen atom; or that when $R_1$ and $R_2$ simultaneously represent a hydrogen atom, n is equal to 1, $R_3$ represents a β-hydroxy ethyl group and $R_4$ represents an amido methyl group, then R is not equal to hydrogen; or that when $R_1$ and $R_2$ represent H, n is equal to 1, $R_3$ represents ethyl, $R_4$ represents $C_1$–$C_6$alkylcarboxymethyl, then R is not equal to H or $CH_3$; or that when $R_1$ and $R_2$ represent H, n is equal to 1, 2, 3 or 4, $R_3$ represents H, $(C_1$–$C_6)$alkyl, $(C_1$–$C_6)$monohydroxyalkyl, $(C_2$–$C_6)$polyhydroxyalkyl, $(C_1$–$C_6)$alkoxy$(C_1$–$C_6)$alkyl or an aminoalkyl whose amine is protected with a $(C_1$–$C_6)$alkylcarbonyl or a methylsulphonyl radical, $R_4$ represents H, $(C_1$–$C_6)$ alkyl, monohydroxy$(C_1$–$C_6)$alkyl, $(C_2$–$C_6)$ polyhydroxyalkyl, $(C_1$–$C_6)$alkoxy$(C_1$–$C_6)$alkyl, $C_1$–$C_6$carboxyalkyl or aminoalkyl whose amine is protected with a $(C_1$–$C_6)$alkylcarbonyl or a methylsulphonyl radical, then R is not equal to H, halogen or $C_1$–$C_6$ alkyl; or that when $R_1$ and $R_2$ represent H, n is equal to 1, $R_3$ represents H or $(C_1$–$C_6)$alkyl, $R_4$ represents H or $(C_1$–$C_6)$alkyl, then R is not equal to H, $(C_1$–$C_6)$alkoxy; or that when $R_3$ and $R_4$ represent H, n is equal to 1, 2, 3 or 4, $R_1$ and $R_2$, independently of one another, represent H, $C_1$–$C_6$alkyl, $C_1$–$C_6$monohydroxyalkyl, $(C_1$–$C_6)$alkoxy$(C_1$–$C_6)$alkyl, $C_2$–$C_6$polyhydroxyalkyl or an aminoalkyl whose amine is protected with a $(C_1$–$C_6)$ alkylcarbonyl or a methylsulphonyl radical, then R is not equal to H, halogen, $C_1$–$C_6$alkyl, or $C_1$–$C_6$alkoxy.

2. A 2-hydroxyalkyl-para-phenylenediamine or an acid addition salt thereof according to claim 1, wherein said halogen is bromine, chlorine, or fluorine.

3. A 2-hydroxyalkyl-para-phenylenediamine or an acid addition salt thereof according to claim 1 chosen from:

2-(β-hydroxyethyl)-5-methylthio-para-phenylenediamine, and an acid addition salt thereof.

4. A 2-hydroxyalkyl-para-phenylenediamine acid addition salt according to claim 1, wherein said acid is selected from hydrochlorides, hydrobromides, sulfates, citrates, succinates, tartrates, lactates, and acetates.

5. A method of preparing an oxidation dye for keratinous fibers comprising including in said oxidation dye at least one oxidation base selected from 2-hyroxyalkyl-para-phenylenediamines and acid addition salts thereof according to claim 1.

6. A method according to claim 5, wherein said keratinous fibers are human keratinous fibers.

7. A method according to claim 6, wherein said human keratinous fibers are hair.

8. A dyeing composition for oxidation dyeing of keratinous fibers comprising, in a medium suitable for dyeing, at least one oxidation base selected from 2-hydroxyalkyl-para-phenylenediamines and acid addition salts thereof according to claim 1.

9. A dyeing composition according to claim 8, wherein said keratinous fibers are human keratinous fibers.

10. A dyeing composition according to claim 8, wherein said human keratinous fibers are hair.

11. A dyeing composition according to claim 8, wherein said at least one oxidation base is present in an amount ranging from 0.0005 to 12% by weight relative to the total weight of said dyeing composition.

12. A dyeing composition according to claim 11, wherein said at least one oxidation base is present in an amount ranging from 0.005 to 6% by weight relative to the total weight of said dyeing composition.

13. A dyeing composition according to claim 8, wherein said medium suitable for dyeing comprises water or water and at least one organic solvent.

14. A dyeing composition according to claim 13, wherein said at least one organic solvent is chosen from $C_1$–$C_4$ lower alkanols, glycerol, glycols and glycol ethers, and aromatic alcohols.

15. A dyeing composition according to claim 14, wherein said at least one organic solvent is present in an amount ranging from 1 to 40% by weight relative to the total weight of said dyeing composition.

16. A dyeing composition according to claim 15, wherein said at least one organic solvent is present in an amount ranging from 5 to 30% by weight relative to the total weight of said dyeing composition.

17. A dyeing composition according to claim 8, wherein said dyeing composition has a pH ranging from 3 to 12.

18. A dyeing composition according to claim 17, wherein said dyeing composition has a pH ranging from 5 to 11.

19. A dyeing composition according to claim 8, wherein said dyeing composition further comprises at least one different oxidation base.

20. A dyeing composition according to claim 8, wherein said dyeing composition further comprises at least one coupler and/or at least one direct dye.

21. A dyeing composition according to claim 20, wherein said at least one coupler is present in an amount ranging from 0.0001 to 10% by weight relative to the total weight of said dyeing composition.

22. A dyeing composition according to claim 21, wherein said at least one coupler is present in an amount ranging from 0.005 to 5% by weight relative to the total weight of said dyeing composition.

23. A dyeing composition according to claim 8, wherein said dyeing composition further comprises at least one cosmetically acceptable adjuvant.

24. A dyeing composition according to claim 8, wherein said dyeing composition is in the form of a liquid, a cream, a gel, or any form appropriate for dyeing keratinous fibers.

25. A kit comprising a first compartment containing at least one dyeing composition according to claim 8 and a second compartment containing an oxidizing composition.

* * * * *

UNITED STATES PATENT AND TRADEMARK OFFICE
CERTIFICATE OF CORRECTION

PATENT NO.     : 6,306,179 B1
DATED          : October 23, 2001
INVENTOR(S)    : Alain Genet et al.

It is certified that error appears in the above-identified patent and that said Letters Patent is hereby corrected as shown below:

<u>Column 28,</u>
Line 53, "nradical" should read -- radical --.

<u>Column 29,</u>
Lines 27 and 28, "methylsuiphonyl" should read -- methylsulphonyl --.
Line 32, "H," should be deleted.
Lines 46 and 47, "phenylened iamine," should read -- phenylenediamine, --.

<u>Column 30,</u>
Line 8, "claim 8" should read -- claim 9 --.

Signed and Sealed this

Fifteenth Day of April, 2003

JAMES E. ROGAN
*Director of the United States Patent and Trademark Office*